United States Patent
Green

(10) Patent No.: US 6,592,890 B1
(45) Date of Patent: Jul. 15, 2003

(54) CONVEYANCE OF ANTI-INFECTIVE ACTIVITY TO WOUND DRESSINGS

(75) Inventor: Terrence R. Green, Lake Oswego, OR (US)

(73) Assignee: OxiBio, Inc., Portland, OR (US)

(*) Notice: Subject to any disclaimer, the term of this patent is extended or adjusted under 35 U.S.C. 154(b) by 0 days.

(21) Appl. No.: 09/694,104

(22) Filed: Oct. 19, 2000

Related U.S. Application Data

(60) Provisional application No. 60/160,521, filed on Oct. 20, 1999.

(51) Int. Cl.[7] .......................... A61L 15/16; A61K 38/44; A61K 33/18
(52) U.S. Cl. ...................... 424/447; 424/445; 424/94.4; 424/667; 424/669
(58) Field of Search ................................ 424/446, 443, 424/94.1, 400, 445, 447, 94.4, 667, 668, 669

(56) References Cited

U.S. PATENT DOCUMENTS

| | | | |
|---|---|---|---|
| 4,576,817 A | 3/1986 | Montgomery et al. | 424/94 |
| 4,783,448 A | 11/1988 | Johansson | 514/57 |
| 5,128,136 A | 7/1992 | Bentley et al. | 424/443 |
| 5,447,505 A * | 9/1995 | Valentine et al. | |
| 5,607,681 A | 3/1997 | Galley et al. | 424/405 |
| 5,888,505 A | 3/1999 | Allen | 424/94.4 |
| 5,928,665 A | 7/1999 | Cercone | 424/445 |
| 6,001,345 A | 12/1999 | Askill et al. | 424/78.25 |
| 6,025,446 A | 2/2000 | Kulkarni et al. | 525/326.9 |

FOREIGN PATENT DOCUMENTS

| | | |
|---|---|---|
| EP | 0 307 376 | 7/1988 |
| GB | 382 572 | 10/1932 |
| WO | WO 85/02422 | 8/1984 |
| WO | WO 93/24132 | 12/1993 |
| WO | WO 96/20019 | 12/1995 |
| WO | WO 96/38548 | 5/1996 |
| WO | WO 99/65538 | 6/1999 |
| WO | WO 00/54593 | 3/2000 |

OTHER PUBLICATIONS

Xie, Y, McDonald MR et al., Mechanism of the Reaction Between Iodate and Iodide Ions in Acid Solutions (Dushman Reaction), *Inorg. Chem.*, 38, 3938–3940, (1999).

* cited by examiner

*Primary Examiner*—Leon B. Lankford, Jr.
*Assistant Examiner*—Ruth A. Davis
(74) *Attorney, Agent, or Firm*—Heller Ehrman White & McAuliffe LLP

(57) ABSTRACT

A wound dressing having anti-infective activity. The wound dressing provides stable and improved formulations of precursors required in generating anti-infective iodine specifically within a wound site where the oxygen tension may be very low. Furthermore, the design of the invention precludes interference by catalase (and other heme proteins.) in competing for hydrogen peroxide where hydrogen peroxide is used as a component of the iodine generating formulation, ensuring more efficient and sustained production of free iodine as a potent anti-infective agent. The invention takes advantage of the physical design of the wound dressing, and the permeation of body fluid into the dressing, which together serve to initiate formation of nascent iodine concomitant with placement of the dressing into, or over, a wound site. The invention circumvents the problem of trapping elemental iodine in the form of tri-iodide, which lacks microbicidal activity, by the chemical method of generating iodine de novo, and in the presence of excess oxidant. Newly formed iodine is thus able to egress and disperse throughout the wound site before there is an opportunity for it to become fully bound as tri-iodide, conferring to the wound site anti-infective activity. Two embodiments of the wound dressing invention are described comprising a mono- and bilayer configuration which, when placed in a wound site, confer to the site anti-infective properties.

15 Claims, 7 Drawing Sheets

CONVEYANCE OF ANTI-INFECTIVE ACTIVITY TO WOUND DRESSINGS

CROSS REFERENCE TO RELATED APPLICATIONS

This application claims the benefit under 35 USC 119(e) of copending Provisional Application No. 60/160,521, filed on Oct. 20, 1999. This application and other documents referred to elsewhere in the specification of this application are incorporated herein by reference in their entireties.

FIELD OF THE INVENTION

The present invention relates to compositions and devices for conferring to wound dressings anti-infective activity.

BACKGROUND OF THE INVENTION

Wound dressings absorb and draw off excess blood, serum and pus in maintaining a clean site conducive to healing. They also aid healing by controlling and restricting water loss. Too much retention of water over the wound site can result in maceration of the skin and impaired healing. Too much loss can lead to hypotherinia and severe electrolyte imbalances, especially in the case of burn patients. Materials used in the manufacture of wound dressings include woven fibers, porous foam pads, and cast hydrogels made up of cellulose and its derivatives (cellulosics), polyesters, nylon, polyacrylamides, polyurethanes, and collagen. The exudation of serum and blood from wounds to the external environment, and the difficulty in maintaining a sterile site, can lead to serious infection because this rich medium when trapped in wound dressings which also maintain a moist environment provides an opportune site for bacterial growth. The definition of a wound dressing as used in this context includes dressings designed to cover compromised skin including tears to the skin caused by blunt trauma, burns, punctures, ulcerations of the skin in which an exudate occurs, etc.

Other conditions at the wound site also occur which promote bacterial growth. First, the bicarbonate buffer system of blood depends upon the dissolution of gaseous carbon dioxide into blood, and its hydration to carbonic acid (catalyzed by carbonic anhydrase present in great abundance in red blood cells) in balancing the blood pH. The equilibrium between the gaseous form of carbon dioxide and bicarbonate lies several thousand fold in favor of the gaseous form of carbon dioxide. In an open wound carbon dioxide is rapidly lost to the atmosphere. This loss of carbon dioxide drives the wound site toward a more alkaline environment, a condition favorable to bacterial growth. Second, the oxygen tension drops precipitously as a consequence of bacterial growth, tissue metabolism, the loss of vascularization and adequate perfusion, and the poor solubility of oxygen across the aqueous interface of the wound site. This is further aggravated by the diffusion barrier of wound dressing materials which restrict free exchange of oxygen. Since the body's phagocytic defense system requires oxygen to generate an anti-infective defense (Klebanoff, S. J. and Clark, R. A. (1978) in *The Neutrophil: Function and Clinical Disorders*, North-Holland Publishing Company, Amsterdam), the decreased availability of oxygen impedes phagocytic killing reactions which otherwise help ward off infections. Although studies show there is an overall drop in the pH of fluid within wound sites by about a half pH unit below the normal blood pH within hours of application of a wound dressing, about a two-fold increase in dissolved carbon dioxide above normal blood levels, and a precipitous drop in oxygen tensions by 10 to 20 fold below that found in normal blood (Ninikoski, J., Heughan, C. and Hunt, T. K. (1971) *Surgery, Gynecology & Obstetrics* 133: 1003–1007; Varghese, M. C. et al. (1986) *Arch Dermatol* 122: 52–57; Katz, S., McGinley, K. and Leyden, J. J. (1986) *Arch Dermatol* 122: 58–62; Sirvio, L. M. and Grussing, D. M. (1989) *J Invest Dermatol* 93: 528–531), this is the result of two opposing reactions: (i) an initial loss of dissolved carbon dioxide from the wound site concomitant with alkalinization of the wound which promotes conditions conducive to bacterial growth and infection; and (ii) a subsequent sharp fall in oxygen tension concomitant with bacterial propagation and tissue respiration coupled with the poor diffusibility of oxygen across the air-water interface of the wound site. Lactic acidosis also ensues. In deep wounds these conditions can create serious, pus loaded abscesses infected with anaerobic bacteria requiring surgery and drainage. In some instances, without proper infection control, life-threatening septicemia may ensue.

Iodine is a potent anti-infective agent with much promise as an affective agent in preventing infections associated with wound care. It has been used for over 150 years in various formulations as a sterilizing agent. Examples include tincture of iodine (an alcoholic solution of free iodine and inorganic iodide), Lugol's solution (a strong mixture of aqueous inorganic iodide and iodine), and in varying complexed forms of elemental iodine using water-soluble iodophors such as polyvinylpyrrolidone (Povidone-iodine) or iodine-bound cadexomers (biodegradable carbohydrate polymer complexes mixed together with elemental iodine formulated in polyethylene glycol). Iodine exists in several oxidation states including its fully reduced iodide ($I^-$) state in addition to its oxidized diatomic free elemental state ($I_2$), and in several higher oxidation states in combination with oxygen (e.g., hypoiodate ($IO^-$), iodate ($IO_3^-$) and periodate ($IO_4^-$)). In aqueous solutions iodide forms an equilibrium complex with elemental iodine, yielding soluble tri-iodide ($I_3^-$), a bound form of iodine devoid of microbicidal activity. Several studies have shown that it is the free form of iodine which exhibits microbicidal activity.

Iodine is difficult to handle in the free form, however, because it is chemically reactive with a number of substances in, and outside, of the body. It is also volatile and readily escapes into the atmosphere. Methods of trapping it in a semistable form involve complexation as an iodophor (e.g. complexed forms of elemental iodine in solution using specific organic binding agents). Among the better known iodofors is Povidone-Iodine, also known as Betadine®, a water soluble polyvinylpyrrolidone organic polymer mixed with inorganic iodide and elemental iodine. In this formulation most of the elemental iodine present binds to the hydrophobic polyvinylpyrrolidone backbone as well as to the cationic pyrrole nitrogen in the form of a tri-iodide complex, none of which forms exhibit any microbicidal activity.

Free elemental iodine is only a small fraction of the total iodine in Povidone-Iodine. 10% Povidone-Iodine, for example, is formulated at ~1% total "available" iodine (e.g., 10,000 ppm). Its free elemental iodine concentration varies from ~0.8 to 1.2 ppm (*Ellenhorn's Medical Toxicology: Diagnosis and Treatment of Human Poisoning*, 2$^{nd}$ edition). LeVeen et al. (*Surgery, Gynecology & Obstetrics* 176:183–190, 1993) have pointed out several deficiencies in Povidone-Iodine formulations for the treatment of wounds including low free elemental iodine levels of marginal efficiency as an anti-infective. They noted that the low level of free iodine is ineffective except against extremely sensitive bacteria. Polyvinylpyrrolidone also contaminates the wound site and has been noted to cause granulomas in wounds. LeVeen et al., and later Shikani and Domb (*J. Amer. College of Surgeons* 183:195–200, 1996), sought to get around these problems by dissolving elemental iodine into polyurethane, a water insoluble polymer with iodine binding properties. Various iodine loaded polyurethane patches have evolved through this approach (U.S. Pat. No. 5,762,638). Iodine impregnated polyurethane dressings are not easily produced with uniform and predictable levels of free iodine, however, as it is difficult to control retention of iodine in a polyurethane polymer base. Iodine trapped in this manner not only diffuses free of the polymer base creating problems regarding shelf-life storage and handling of the wound dressing material, but it is also reactive and can be consumed before it comes into contact with wound fluid.

Alternative approaches for sequestering free iodine have included its complexation in biodegradable carbohydrate polymeric hydrogels (U.S. Pat. No. 4,783,448; U.S. Pat. No. 4,010,259). In the latter hydrogel formulations, the iodine content is stated to preferably range from a low of about 0.4% to about 2% (wet weight of gel). These formulations are unstable for the same reasons that Povidone-iodine is unstable.

There are other significant drawbacks inherent in the formulation of these iodofor wound dressings. The high iodine content poses a serious toxicological limitation in their application, especially regarding their use over large surface areas of the body. This is because iodine, formulated in these types of dressings, is readily absorbed by the body and concentrated in the thyroid gland. Excess iodine taken into the body leads to hypothyroidism through a shutdown and atrophy of the thyroid gland. Whereas the essential daily intake needs of the body for iodine is in the range of 150 to 200 micrograms per day, and the upper safe threshold is believed to be no greater than about 1000 micrograms per day (Ensininger, A. H. et al. (1993) in *Foods and Nutrition Encylopedia*, $2^{nd}$ edition, CRC Press), it takes very little exposure to iodofor formulations to exceed this level of intake. For example, a one gram formulation containing 0.4% by weight iodine complexed in a carbohydrate polymer (U.S. Pat. Nos. 4,010,259 and 4,783,448) is the equivalent of 4,000 micrograms (e.g., 0.004 grams) total iodine, or an amount four times the recommended upper daily safe intake threshold. For Povidone-iodine impregnated bandages, the high total iodine content (e.g., 10%) likewise restricts the use of these formulations to very small areas of the body, and for limited duration.

Montgomery et al. (U.S. Pat. No. 4,576,817) claim the use of glucose oxidase in combination with lactoperoxidase and iodide as a potent anti-infective wound dressing through formation of hypoiodite. They provide neither data nor information as to how hypoiodite, the end-product formed, could be made in a wound site lacking significant oxygen tensions required for the formation of hydrogen peroxide. This is problematic since oxygen is an obligatory substrate in the scheme proposed in their patent. Furthermore, while acknowledging that catalase present in a wound site competes for hydrogen peroxide formed by the glucose oxidase reaction, they propose (but do not demonstrate) that levels of ascorbic acid added to their formulation in the range of from about 1 to 100 nanomoles per gram of material should be sufficient to block degradation of hydrogen peroxide required by lactoperoxidase in catalyzing formation of hypoiodite. They also propose adding iron. salts such as ferrous sulfate into the absorbent material of their wound dressings to potentiate ascorbate mediated inhibition of catalase. It is well-known, however, that the combination of iron salts and ascorbic acid in the presence of hydrogen peroxide generates hydroxyl radicals (Fenton chemistry), and that hydroxyl radicals attack multiple biological sites indiscriminately. Hence the scheme outlined by Montgomery et al. in U.S. Pat. No. 4,576,817 would not ensure selective inhibition of catalase, but rather inactivation of any enzyme (including glucose oxidase and lactoperoxidase) coming into contact with the short-lived, but powerful hydroxyl radical oxidizing agent. Other limitations include: (i) competition by hemoglobin (a pseudoperoxidase) in consuming hydrogen peroxide; (ii) the instability of ferrous salts in aqueous solution and conversion to insoluble ferric hydroxide complexes which precludes any anticipated lasting effect of this formulation as far as a role of ferrous salts is concerned; and (iii) the rapid and aggravating depletion of dissolved oxygen in a wound site environment caused by dissolution of ferrous salt into wound fluid as a result of the well-known spontaneous reaction of the ferrous salt with dissolved oxygen in solution.

EP 0 307 376 A1 similarly proposes to use oxidoreductases in combination with a peroxidase and inorganic iodide, or an alternate hydrogen peroxide source such as magnesium or percarbamide, to be formulated in the pH range of from about 3.5 to 6.0, as a wound dressing treatment. Aside from the limitations already noted in generating hydrogen peroxide in a semi-anaerobic environment, there is no explanation in EP 0307376A1 as to how the formulation is presented in a wound dressing. The compositions proposed are described only as ". . . a pure dry pulverulent mixture" or "in the form of tablets and granules as well as double layer tablets which are dissolved . . . " In using magnesium or percarbamide as the hydrogen source, the patent does not address how hydrogen peroxide released would be spared degradation by catalase and other heme proteins common to the wound site.

SUMMARY OF THE INVENTION

The invention is directed to a wound dressing having anti-infective activity. In one embodiment the wound dressing generally comprises a sheet comprising a crosslinked polymeric matrix, and an oxidant generating formulation contained within or on the polymeric matrix, the polymeric matrix being impermeable to reactants such as bacteria, catalase, and proteins, present in the wound site. The polymeric matrix is impermeable to the reactants from the from the body fluid which would be capable of reacting with hydrogen peroxide and oxygen in the sheet. In one embodiment, the crosslinked polymeric matrix comprises polyacrylamide. In aspect of the invention, the oxidant generating formulation is stable at least until contacted by a substrate, such as glucose, which is permeable into the polymeric matrix from the patient's body fluid at the wound site. In a presently preferred embodiment, the anti-infective oxidant generated by the oxidant generating formulation is elemental iodine.

In one embodiment, the wound dressing of the invention is a single, or "mono" layer. In the monolayer embodiment, the dressing has the oxidant generating formulation, or at least a part thereof, in a single layer. However, the single layer may comprise a plurality of stacked layers, provided the plurality of layers all have the same composition. In an alternative embodiment, the wound dressing is multilayered having a first part of the oxidant generating formulation in a first layer, and a second part of the oxidant generating formulation in one or more additional layers.

In one embodiment of the invention, the multilayered wound dressing generally comprises a first sheet having an iodide, an oxidant or oxidant generator impregnated therein and a second sheet having a proton donor. In one embodiment, the first sheet comprises a hydrophobic polymer having a microcannular structure releasably containing the iodide and oxidant or oxidant generator. In another embodiment, at least one of the first and second sheet comprises a lyophilized hydrogel.

The present invention provides for stable and improved formulations of precursors required in generating anti-infective iodine specifically within a wound site where the oxygen tension may be very low. Furthermore, the design of the invention precludes interference by catalase (and other heme proteins) in competing for hydrogen peroxide where hydrogen peroxide is used as a component of the iodine generating formulation, ensuring more efficient and sustained production of free iodine as a potent anti-infective agent. The invention takes advantage of the physical design of the wound dressing, and the permeation of body fluid into the dressing, which together serve to initiate formation of nascent iodine concomitant with placement of the dressing into, or over, a wound site. The invention circumvents the problem of trapping elemental iodine in the form of tri-iodide, which lacks microbicidal activity, by the chemical method of generating iodine de novo, and in the presence of excess oxidant. Newly formed iodine is thus able to egress and disperse throughout the wound site before there is an opportunity for it to become fully bound as tri-iodide, conferring to the wound site anti-infective activity. Two embodiments of the wound dressing invention are described comprising a mono- and bilayer configuration which, when placed in a wound site, confer to the site anti-infective properties.

DETAILED DESCRIPTION OF THE INVENTION

Figure 1:
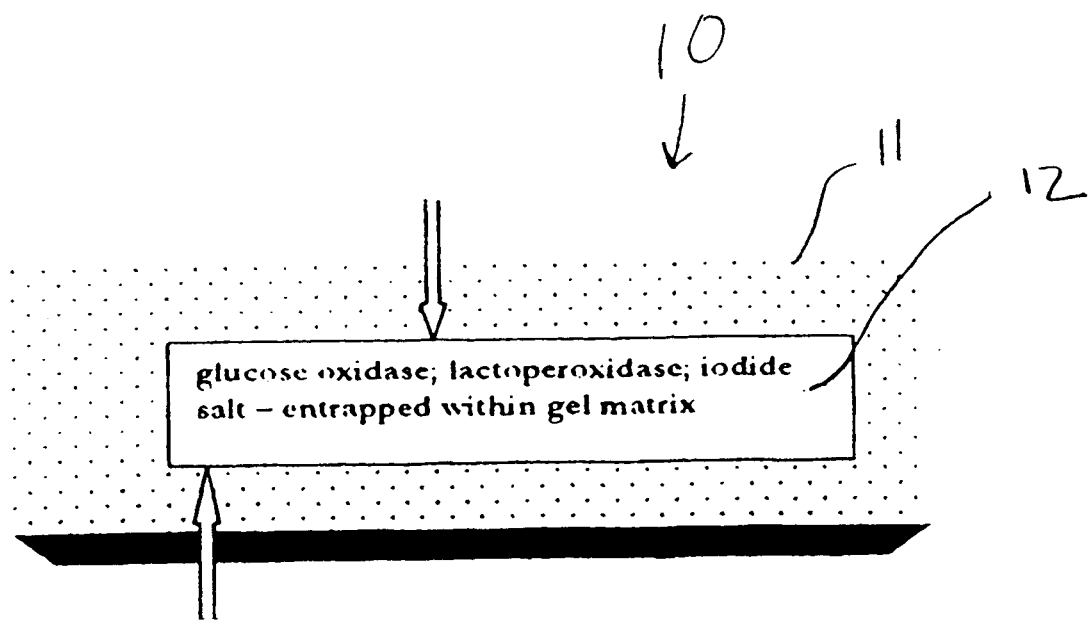
FIG. 1 illustrates a side view of a schematic diagram of a monolayer wound dressing which embodies features of the invention.

Iodine Generating Chemistry and Fabrication of the Monolayer Dressing

Iodine is formed on demand, as needed, upon application of the wound dressing to a wound site by the composition of the iodine generating formulations, and by the physical composition and layout of wound dressing materials. In both the mono- and bilayer embodiments of the invention iodine generating formulations are placed within the wound dressing in stable form. Iodine formation only ensues when the wound dressing is activated (e.g., put into use). Varying methods and formulations for iodine production have been described in prior art (U.S. Pat. Nos. 4,278,548, 4,312,833, 4,476,108, 5,232,914, 5,607,681, 5,648,075, 5,849,241). These methods have in common the presentation of inorganic iodide, an oxidant (either enzymatic or inorganic), a proton source and water as a solvating agent in combination to affect formation of free elemental iodine through oxidation and conversion of iodide into iodine as outlined in equation 1:

$$H^+ + I^- + \text{Oxidant} \rightarrow I_2 + H_2O \tag{1}$$

If any one of the three components is missing, iodine formation cannot ensue. In the present invention, advantage is taken of this observation. De novo formation of iodine on demand is thus regulated by restricting the complete reaction sequence from occurring by controlling access to these essential components in the wound dressing formulation until presentation of the wound dressing to a wound site. The oxidant may be a metal oxide of iodine such as potassium or sodium iodate. Alternatively, the oxidant may be magnesium peroxide, calcium peroxide, percarbamide, perborate, an organo peroxide. It may be formed enzymatically as hydrogen peroxide by an oxidoreductase such as glucose oxidase, galactose oxidase, cholesterol oxidase, and similar types of oxidoreductases. Alternatively, a reducing substance present in the body fluid, such as glutathione, vitamin C, and uric acid, react with oxidant generating formulations to produce the anti-infective oxidant. For example, in one embodiment, the oxidant generating formulation is an oxidant such as iodate, and a proton source, which reacts with a reducing substance to generate anti-infective elemental iodine. A variety of suitable proton sources may be used including oxidoreductase, a lipase, an esterase, and weak acids such as citric acid, lactic acid, fatty acids and other carboxylic acids with a pKa in the range of from about 2 to about 5.

In the monolayer embodiment, in the case where an oxidoreductase is used to generate the oxidant necessary in catalyzing iodine generation, an organic substrate in combination with oxygen serve as precursors in catalyzing formation of hydrogen peroxide. In combination with horseradish or lactoperoxidase, this allows for the oxidation of iodide to free elemental iodine. The substrate present in the wound site creates an "on demand" activation of the wound dressing for formation of anti-infective free elemental iodine. All of the other essential reactants are formulated within a single dressing wherein the initiating substrate, in the wound fluid, completes the reaction sequence allowing for iodine formation to ensue. In embodiments where hydrogen peroxide is a key element of the reaction sequence, catalase and other hemeproteins present in the wound site pose a significant source of interference, as noted earlier, in competing for the available hydrogen peroxide. Provisions are therefore included in the design of the wound dressing (see below) to keep hydrogen peroxide separate and localized together with the other essential precursors required for de novo formation of iodine within the body of the wound dressing. Once iodine is formed, it is free to diffuse inward and to the periphery of the wound site where catalase and other heme proteins may be found, but which then pose no problem, conferring then to the wound site anti-infective activity.

The monolayer dressing is constructed so at to restrict and control the site and means by which iodine can be generated. In the first (see FIG. 1), the wound dressing is fabricated from cross-linked polyacrylamide as described in U.S. Pat. No. 5,196,190 as a single layer of film, or patch, to be applied directly to the wound site. The concentration of the cross-linking agent relative to the monomer used in fabrication of the gel matrix is chosen so as to entrap reactants such as oxidoreductase and peroxidase required for generation of iodine within the body of the wound dressing. Proteins in the wound site, such as catalase and other heme proteins, cannot enter the body of the wound dressing in this embodiment because they cannot pass through the pores of the wound dressing matrix fabricated out of acrylamide. They are sterically too large to access this environment. FIG. 1 illustrates the basic archictecture of the monolayer dressing. Techniques for constructing molecular sieving gels in restricting protein migration in this manner are well-known (Blackshear, P. J. (1984) *Meth Enzymol* 104: 237–255). Hence, by adjusting the amount of bis-acrylamide crosslinker relative to the monomer acrylamide, the oxidizing enzymes required for generation of iodine remain separated from wound site proteins.

FIG. 1 illustrates a side view of a schematic diagram of a monolayer wound dressing 10 which embodies features of the invention, generally comprising a polymeric sheet 11 fabricated from acrylamide with restricted pores designed to retain the oxidant generating formulation 12 entrapped therein. For example, in one embodiment, an oxidant generating formulation entrapped in the acrylamide crosslinked sheet, which generates elemental iodine, comprises glucose oxidase, lactoperoxidase, and iodide salt. Large molecular weight interfering substances present in the wound fluid such as catalase, other heme proteins and bacteria are sterically hindered from penetrating the body of the wound dressing where iodine is formed. Glucose from the wound site (see lower arrow) freely permeates and initiates iodine formation within the body of the dressing. Oxygen (see upper arrow), the cosubstrate of the glucose oxidase reaction in this example, freely diffuses into the wound dressing from the exterior side opposite that of the wound fluid.

After trapping the essential enzyme reactants within the body of the acrylamide dressing during casting of the gel dressing, the dressing is soaked and washed in a dilute iodide solution and processed for packaging as outlined in U.S. Pat. No. 5,196,190. In this embodiment of the wound dressing, glucose, for example, present in blood and serum as a natural body fluid constituent in the wound site, because of its low molecular weight, freely diffuses into the wound dressing upon application of the dressing to a wound site. There it becomes oxidized by glucose oxidase (the chosen oxidoreductase) which in turn allows for elemental iodine formation to occur through the action of lactoperoxidase on hydrogen peroxide (also embedded in the dressing), formed de novo, and iodide, the former a product of the glucose oxidase reaction, and the latter preloaded during fabrication of the gel dressing. Neither bacteria nor other enzyme systems capable of competing for oxygen are present in the body of the wound dressing. Thus the oxygen tension in the wound dressing is markedly better than in the wound fluid environment where restricted diffusion of oxygen and competing routes of oxygen consumption both conspire to bring the oxygen tension to near anaerobic conditions.

A variation of this embodiment involves entrapment of a polymeric proton donor within the wound dressing together with the oxidoreductase and peroxidase. Examples of polymeric proton donors include carboxymethylcelluloses, pectins, alginic acid, or, for example, various linear and cross-linked polyacrylates available commercially such as B. F. Goodrich Carbopol 971 PNF, Carbopol 974, or Noveon AA1. In this manner, while the organic substrate (vis., glucose) of the oxidoreductase permeates from the wound site into the wound dressing, and once there initiates formation of hydrogen peroxide and iodine, the presence of protons also entrapped in the dressing enhances the rate and efficiency of iodine production.

Alternatively, using a different embodiment of the monolayer dressing, the formation of iodine can be affected by using preformed oxidants such as calcium or magnesium peroxide, percarbamide, iodate, or perborate in combination with a suitable proton generating system incorporated within the body of the acrylamide wound dressing. In this embodiment, a proton generator is required to drive formation of iodine, initiated by a substance(s) present in the wound site. The proton generator may be the oxidoreductase entrapped within the dressing during casting of the gel with catalase substituted in place of peroxidase in the gel dressing. Alternate acceptable proton generators to be used include lipases, or esterases, wherein hydrolysis of the lipase/esterase substrates release protons which dissociate, driving formation of free iodine. In the case of an oxidoreductase, after entrapping within the body of the wound dressing the oxidoreductase, and catalase, and then loading inorganic iodide, and oxidant (vis., sodium iodate) into the dressing, the gel is processed and stored for future use as needed. Upon placement on a wound site it forms iodine as the substrate of the oxidoreductase diffuses into the wound dressing. Iodine can only form in the dressing as protons are generated via the action of the entrapped oxidoreductase on its substrate. This serves as the initiating event for formation of iodine. Catalase in this embodiment serves to break down hydrogen peroxide to oxygen and water, improving the efficiency of the oxidoreductase in converting its organic substrate to an acid (e.g., proton generating) donor by recycling some of the oxygen consumed in the formation of hydrogen peroxide back to the oxidoreductase.

Since the reaction depends upon protons in driving iodine formation, sustained iodine formation can be maintained by controlling proton generation, or its release, in the wound dressing. The following equations illustrates the dependency of the iodine generating formulation on protons. In this illustration, glucose oxidase represents the mechanism of generating protons required for subsequent formation of iodine

Glucose+$O_2$→Gluconic acid+$H_2O_2$

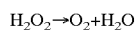
$H_2O_2$→$O_2$+$H_2O$

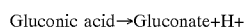
Gluconic acid→Gluconate+$H^+$

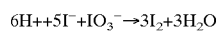
$6H^+ + 5I^- + IO_3^- \rightarrow 3I_2 + 3H_2O$

Glucose is derived from the wound site, permeates the wound dressing, and is converted within the wound dressing to gluconic acid (the proton source). The pKa of gluconic acid is approximately 4.0, sufficiently low so that gluconic acid dissociates to yield protons which drive the oxidation and conversion of iodide into free iodine. Iodate is the oxidizing agent. Hence, the invention relies upon oxygen consumption occurring at the air interface of the wound dressing. This generates protons. Protons formed in this manner diffuse inward into and throughout the dressing causing the formation of elemental iodine at sites where the oxygen tension may be at or near zero. The reaction scheme is self-limiting in that protons supplied in the proton generating stage of the reaction sequence are consumed in the formation of iodine. Protons produced under anaerobic conditions, either from bacteria or by lactic acidosis, will also initiate iodine formation as they diffuse into the wound dressing.

Iodine Generating Chemistry and Fabrication of the Monolayer Dressing

Figure 2A:
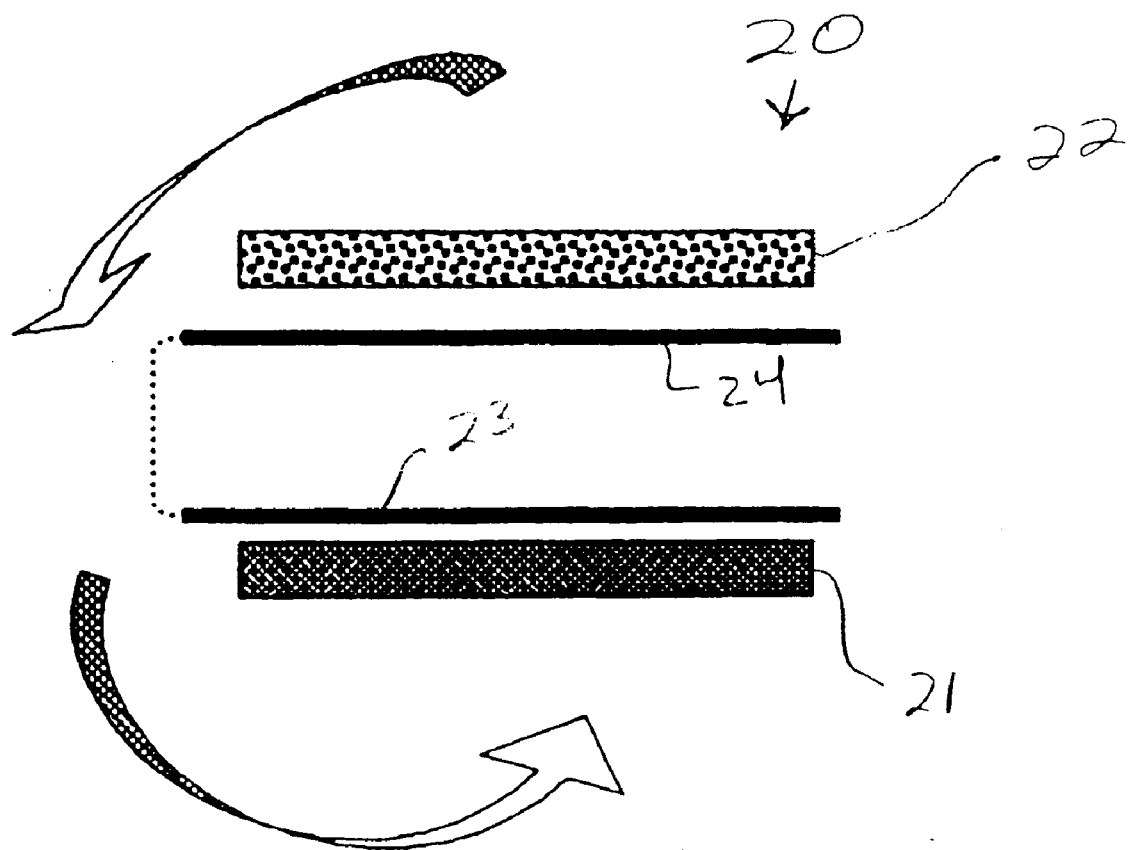
FIGS. 2A and 2B illustrate a side view of a schematic diagram of a bilayer wound dressing which embodies features of the invention.
Figure 2B:
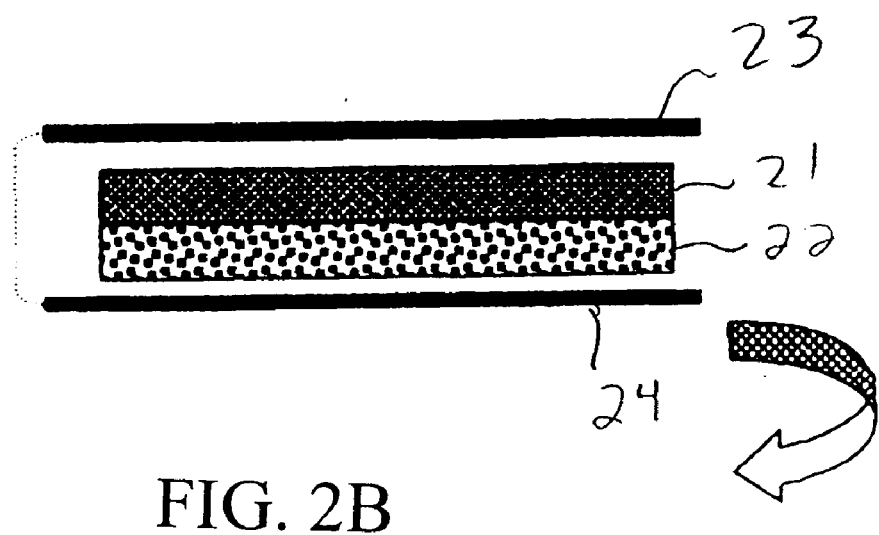

An alternate bilayer configuration in the fabrication of the wound dressing is shown in FIGS. 2A and 2B. In this embodiment of the invention the wound dressing is fabricated as a bilayer wherein one layer contains some of the essential reactants required as illustrated in equation 1, and the remaining reactants are contained within the second layer. Each layer is fabricated and loaded with reactants, and placed on a thin lamellar film made up of polyurethane, polyethylene, or any other convenient water impenetrable film in a configuration so that just prior to use the two layers may be placed together for layering as a composite sandwich over the wound site. The precise configuration of the film layers is not critical. Adhesive materials may be included so that as the two layers are brought together they are caused to adhere to one another, or they may be constructed to fit together in a "lock and Key" configuration when brought together. Alternatively, the two films may be allowed to simply reside near one another in the wound site, held in place by a wrapping placed over the top of the layers as they are placed into, or over, the wound site. The bilayer configuration of the wound dressing allows for activation of iodine generation when the two layers are brought into proximity with one another. Mixing of the reactants is enhanced with fluid from the wound permeating into the two layers which brings reactants together in initiating de novo formation of iodine. In the embodiment shown in FIGS. 2A and 2B, which illustrates a side view of a schematic illustration of a bilayer wound dressing 20, a first layer 21 contains iodide and an oxidant, and a second layer 22 contains a proton source. Thus, essential reactants for generation of nascent iodine are partitioned between the two layers, each placed on a water impermeable platform 23/24 and positioned so that at the time of activation the two layers are brought into contact with one another (see arrows). FIG. 2a illustrates the layers 21/22 before being brought together, and FIG. 2a illustrates the layers 21/22 after being brought together. The backing platform 24 is removed from the "Proton Source" layer in this example (see arrow) so that the dressing can then be inserted onto the wound site. The platform 23 covering the "Iodide+Oxidant" layer may be left in place, or peeled away as desired. The dashed line represents a perforation point-where the two layers 21/22 can be easily separated.

In the design illustrated in FIGS. 2A and 2B, the "proton donating" layer is rotated under the lower layer containing iodide (see arrows) just prior to placement on the wound site. The nonadhesive lamellar backing is peeled away from the "proton donating" layer, and the bilayer sandwich then placed over the wound site with the proton source entering the wound fluid first. The lammelar backing can then be removed and discarded from the upper layer containing iodide. Alternatively, the backing can be perforated so that the lower lammelar portion covering the proton donating source is removed, leaving the upper lammelar covering as part of the backing (e.g., a top covering) of the wound dressing. An adhesive may be added to the periphery of the upper lammelar backing, if desired, to serve for attachment of the dressing to skin surrounding the wound site to be covered.

The bilayer design allows for direct activation of the wound dressings as the two layers are brought together and wetted, either by body fluid, or by water introduced to the dressing during its application. Fluid permeating the layers brings the reactants together from which anti-infective iodine can then be formed as in equation 1.

An advantage of the bilayer technique is that formulations of iodide and iodate, or alternate oxidizing agents of iodide, can be encapsulated in a thin polymer comprising the upper layer. This allows for the sustained release of iodide and oxidizing agent over extended periods of time, and in low levels sufficient to allow for iodine formation when these reactants encounter the proton rich second layer of the bilayer embodiment of this invention while minimizing the potential toxicity of too much iodine being delivered to the wound site in a single bolus. In addition, the upper and lower wound dressing films used in the bilayer embodiment need not be restricted to a single wound dressing material. The upper layer may be fabricated, for example, out of polyurethane or silicone with iodide and the oxidizing agent (vis., iodate) mixed as a finely ground solid suspension into the polymer base prior to casting and curing of the polymer. Films cut from this layer may then be combined with an acrylamide film cast and impregnated with a proton donating source. A film of polyurethane or silicone containing the proton donor encapsulated in a similar manner to that of the first film may be substituted in place of the acrylamide polymer. Alternatively, a lyophilized hydrogel formulation comprising carboxymethcellulose, carbopol polymers, alginic acid, with various other hydrogels mixed into the film to provide desired physical properties with regard to the viscosity and other mechanical properties of the gel upon hydration within the wound site, adjusted to a pH prior to lyophililzation between about 3.5 and 6.0, preferably about pH 4.5 to 5.0, may be used as the second "proton donating" layer. Citrate, or phosphate, may also be included in the hydrogel formulations to ensure maintenance of the preferred pH optimal for driving formation of iodine as precursors of iodine formation are slowly released from the upper iodide donating layer.

Incorporation of Formulations Into the Wound Dressing Layers

For fabrication of acylamide wound dressing layers reference should be made to U.S. Pat. No. 5,196,190. Enzymes and proton donor polymers to be incorporated into the acrylamide gel are premixed into the monomer suspension before casting of the gel at concentrations comparable to those listed for the preparation of hydrogels (see below). The impregnation of the acrylamide gels with iodide and/or inorganic oxidants is similarly at concentrations comparable to those used in hydrogel formulations. Where the iodide and oxidant formulations are to be included in a hydrophobic polymer layer, a detailed description for the preparation of slow release formulations is as follows: In the oxidative conversion of iodide into iodine, a wide array of oxidants, i.e., oxidizing agents, may be encapsulated into a hydrophobic polymer base so long as they can be formulated into an anhydrous powder. The oxidants remain immiscible upon addition to the hydrophobic polymer used in fabricating the delivery device, and they retain the capacity to solvate upon immersion in aqueous fluids so that they can come into contact with iodide, and thereby cause its conversion to iodine. In the case of sodium iodate, or iodine pentoxide (which spontaneously hydrolyzes to iodate), crystalline salts become entrapped in microcannulae of the membrane layer and egress upon coming into contact with body fluid such as wound fluid. The crystalline salts react with reducing compounds present in the wound fluids, resulting in elemental iodine formation in accordance with redox reactions involving iodine chemistry. Hence, the use of iodate in formulations exploits the reducing environment in which the device resides to allow for elemental iodine formation to ensue, bathing the wound with microbicidal iodine activity (e.g., from 5 to 100 ppm).

For incorporation of formulations into hydrophobic polymers, fabrication of the layer requires that the iodine-generating formulation first is ground to a fine powder of 200 micron, or less. The dry formulation is then mechanically mixed at room temperature (20 to 25° C.) into a hydrophobic elastomer, such as described below. The formation of iodine in this embodiment of the invention can then ensue as fluid from the wound site permeates into the microannular spaces of the polymer base formed by entrapment of the solid mixture in the polymer base. This allows for the release of nascent iodine from the polymer into the wound site while minimizing the release of iodide salts which to a large extent remain trapped within the microcannular structure of the hydrophobic polymer formed in this fashion. Variations in producing master batches prior to curing in the final polymer base are amenable to the technology. For example, the anti-infective oxidant generating component such as potassium iodide may be premixed in one co-polymer (Part A). The proton source such as monosodium phosphate and an oxidizing agent such as sodium iodate can then be mixed into the other co-polymer crosslinking agent together with an appropriate catalyst (Part B). To cure the polymer, Part A and Part B are then mixed together allowing for initiation of the crosslinking polymerization process concomitant with encapsulation of the iodine-generating formulation within the final mixture. Before the mixture has fully cured, the mixture is delivered to a mold, or extruded from a dye, and cured to its final configuration. The product formed can be extruded as a fine thread like material to be woven into a mat, or extruded as sheets to be cut to the desired configuration for a specific wound care application. In thermoset polymers the iodine generating formulations can be mixed into the polymer upon heating the polymer slightly above its melting point so that upon cooling a uniform dispersion is obtained. Suitable hydrophobic polymers (elastomers) to be used in fabrication of the hydrophobic layer include, for example, medical grade Low Consistency Silicone elastomers (LSR silicone elastomers) such as NuSil MED-4815, -4820, -4830, -4840 or -4850 molding materials, NuSil medical grade LSR4-5805 silicone elastomer, High Consistency Silicone Elastomers (HTR elastomers) suitable for extrusion such as NuSil MED-4550, -4565, -4719, -4750 and -4780, as well as thermoplastic and room temperature vulcanization silicone polymers. Other suitable polymers include elastomers such as polyurea, polyurethane, ethylene vinyl acetate, polyvinylchloride, polyesters, polyamides, polycarbonate, polyethylene, polymethyl methacrylate, cellulose esters such as ethyl, methyl and propyl forms, polypropylene, polystyrene, polytetrafluoroethylene, poly(ethylenevinyl acetate), elastomeric organosilicon polymers, poly(hydroxyl alkyl esters), copolymers and thermoplastic hydrophobic combinations thereof.

The high curing and melt temperatures, in the range of from 120 to 230° C., pose no problem for entrapment of components of the formulations used in the fabrication process. The free level of iodine formed at the surface of the layer embodiment upon wetting and activation of the iodine generating chemistry in a body fluid should preferably reach a level not less than ~5 ppm, or in excess of about 100 ppm within 20 minutes of its exposure to body fluid. This level of elemental iodine is highly desirable to confer to the device microbial and virucidal activities.

Alternatively, the inventive device may be fabricated from a hydrophilic (e.g., hydrogel) polymer. In this embodiment, the polymer base serves to encapsulate the iodine generating formulation and solvates concomitantly with activation of the iodine generating formulation as a gel-sol, mucoid-like product, coating and bathing the wound site with anti-infective activity.

Suitable hydrogels for mixing into formulations include, for example, from about 0.2 to 5% high or medium viscosity alginic acid, B. F. Goodrich Carbopol 971 PNF (or crosslinked analogues of this polyacrylic acid such as B. F. Goodrich Carbopol 974 PNF or Noveon™ AA1), or about 1:1 mixtures of alginic acid and Carbopol, adjusted from to a preferred pH of about 3.7 to 5.0 with NaOH. Several classes of hydrogels are amenable to this embodiment, in general, including hydrogels selected from groups consisting of linear or cross-linked polyacrylates, polycarboxyalkyl celluloses, hydroxyalkyl celluloses, water soluble celluloses, polyethylene or polyvinyl alcohols, chitosan polymers, as well as salts of alginic acids and combinations thereof.

Providing for a low pH in the hydrogel embodiment of the device is important in ensuring a steady supply of $H^+$ in forming nascent elemental iodine. The low pH has an additional advantage in that it also confers some microbicidal activity to the hydrogel formulation. The hydrophilic polymers (e.g., hydrogels) containing the elemental iodine generating formulations must first be premixed at low temperatures near the freezing point of water. They can then be transferred to a mold, and frozen and lyophilized to remove water, forming an anhydrous, stable formulation, preferably in the shape of a flat sheet that can be cut and pressed for construction of the bilayer embodiment of the wound dressing. This process of freezing and then lyophilizing the formulation yields a sponge-like product capable of producing microbicidal nascent elemental iodine when the hydrogel is applied on a wound site. At the wound site, the sheet solvates to a thick gel, adhering tightly to epithelial cells with the consistency of a thick mucous-like substance, releasing the active ingredients by which elemental iodine can then be formed. The anhydrous formulation is stable and can be stored for extended periods without loss of iodine generating activity so long as it remains dry.

Iodide and oxidizing agents of iodide such as iodate salts, or enzyme oxidases such as glucose oxidase (D-glucose:oxygen 1-oxidoreductase; EC 1.1.3.4) and peroxidase (donor:hydrogen-peroxide oxidoreductase; EC 1.11.1.7), may be mixed together and formulated into a single hydrogel formulation, or the iodide and oxidizing agents may be cast in separate hydrogel formulations, and, once recovered in lyophilized form, reassembled as a bilayer of iodide and oxidizing agent.

The freeze-drying technique for fabrication of the hydrogel embodiment of the inventive layer allows for fabrication of a dissolvable, anti-infective, hydrogel formulation. The sponge-like hydrogel product can be pressed into sheets, or rolls, and cut into various shapes, by placing the lyophilized hydrogel product in a hydraulic press and applying a pressure of not less than 100 lbs per square inch, nor more than 12,000 lbs per square inch to the final product. This yields a fine, paper-like product which can be cut and shaped as desired, and which upon wetting rehydrates to a gel solution.

A bilayer hydrogel dressing can be formed for application to an infected site by layering one hydrogel sponge product containing iodide on top of a second containing the oxidizing agent, placing the composite product into a hydraulic press, and by then applying pressure to the layers to form a bilayer membrane. The wetting of the sandwich product results in solvation of the hydrogel, and concomitant production of anti-infective iodine.

Formulations used in the wound dressing layers are comprised of iodide, wherein the iodide is selected from the group of potassium iodide, sodium iodide and combinations thereof, an oxidizing agent, wherein the oxidizing agent is selected from the group consisting of alkali iodine oxide salts such as sodium iodate, iodine pentoxide, other inorganic or organic oxidizing agents, peracids (e.g., perborate, peracetate, etc.), and combinations thereof. Alternatively, the oxidizing agent is replaced by $H_2O_2$ generating enzyme oxidases, such as glucose oxidase (beta-D-glucose:oxygen 1-oxidoreductase; EC 1.1.3.4) or diamine oxidase (amine:oxygen oxidoreductase[deaminating] [pyridoxal-containing]; EC 1.4.3.6), facilitated by the addition of peroxidase (donor:hydrogen-peroxide oxidoreductase; EC 1.11.1.7), and combinations thereof. The concentration of iodide in the aqueous formulations should be not less than about 0.1 mM or more than about 200 mM. The oxidizing agent acting on iodide may be chosen from alkali oxides of iodine such as sodium iodate, or iodine pentoxide, or peracids made up in solution prior to lyophilization and reconstitution to not less than 0.1 mM nor more than 200 mM.

In the embodiment in which the $H_2O_2$ generating enzyme oxidases is substituted in place of the inorganic or organic oxidizing agents, glucose oxidase, for example, may be made up in solution prior to lyophilization at a concentration of at least 2 μg/ml wherein its specific activity is in the range of 2,000 to 200,000 IU per gram of solid. Peroxidase may be incorporated into the formulation to facilitate the oxidative conversion of iodide to iodine made up at a concentration of at least 2 μg/ml, wherein its specific activity is in the range of 250,000 to 330,000 IU per gram of solid, or diamine oxidase (amine:oxygen oxidoreductase[deaminating] [pyridoxal-containing]; EC 1.4.3.6) may be substituted in place of glucose oxidase made up to at least 2 μg/ml wherein its specific activity is in the range of 50 to 800 IU per gram of solid, or any combination thereof.

In addition to these reactive ingredients, the formulations are optionally supplemented with a hydrogel agent, wherein the hydrogel agent is selected from the group consisting of linear polyacrylates, cross-linked polyacrylates, polycarboxyalkyl celluloses, polyalkyl celluloses, hydroxyalkyl celluloses, water soluble celluloses, polyethylene or vinyl alcohols, chitosan polymers, salts of alginic acids, and combinations thereof. The hydrogel is preferably made up to not less than about 0.2% (by weight) in water, nor more than about 5% by weight. Preferably, the hydrogel is about 2% by weight of the composition. Preferably, the pH is adjusted to a range of not less than about 2.0 and not greater than about 6.5. Most preferably, the pH is about 4.5. Examples of specific hydrogels suitable for use include cross-linked polyacrylates, such as Polycarbopol 974 PNF or Noveon™ AA1 (B. F. Goodrich), crab shell solubilized chitosan (poly-[1→4]-β-D-glucosamine), carboxyethyl- and methyl cellulose polymers, and sodium salts of alginic acid (ranging from high to medium viscosity −2% solution at 25° C. equivalent ranging from 14,000 cps to 3,500 cps, respectively).

In fabricating the inventive wound dressing layer from hydrophobic polymers, the same basic iodine generating formulations used as in hydrogel delivery devices, excluding hydrogels in the final formulations, and water (aqueous solvent or salts thereof), can be used. Formulations are mixed and slurried into hydrophobic polymers used in fabricating the device in the form of anhydrous powders, ground to less than 200 microns, which after mixing and curing, form microcannula within the fabricated device from which the ingredients can then react upon solvation with exposure of the device to body fluids. The dry iodine-generating component is a mixture of an iodine salt selected from the group consisting of anhydrous alkali iodine salts such as potassium or sodium iodide at a concentration of from about 0.01% to about 16% (by weight), and an oxidizing agent, wherein the oxidizing agent is selected from the group consisting of anhydrous alkali iodine oxide salts such as sodium iodate, or iodine pentoxide, or a peracid or its salt, such as perborate, organoperoxy acids, and the like, at a concentration of from about 0.01% to about 16% (by weight).

It should be noted that the glucose oxidase/peroxidase elemental iodine generating formulations with omission of glucose from the polymer base confer substrate (i.e., glucose) specificity to the inventive device. In the absence of glucose (such as when the device is stored ready for use) the formulation cannot catalyze formation of nascent elemental iodine because glucose is an essential first step component of the chemical reactions leading to elemental iodine formation. This particular formulation allows for the device to activate and lay down anti-infective activity only upon contact with body fluids containing glucose.

Examples of suitable hydrogel polymers include from 0.5 to 2% high or medium viscosity alginic acid, B. F. Goodrich Carbopol 971 PNF (or crosslinked analogues of this polyacrylic acid such as B. F. Goodrich Carbopol 971 PNF or Noveon™ AA1), or 1:1 mixtures of alginic acid and Carbopol, adjusted from a pH of about 3.7 to 5.0 with NaOH. The low pH of the hydrogel is important in providing H which are consumed in forming nascent elemental iodine, and in maintaining the pH of the wound fluid from about 3.7 to 5.0. The low pH has an additional advantage in that it also confers some microbicidal activity to the hydrogel formulation.

Critical fabrication steps of the hydrogel device to encapsulate the elemental iodine generating formulations include: (1) prechilling the gel-forming solution to less than 4° C. but not below freezing temperatures; (2) adding and mixing in an elemental iodine generating formulation into the gel solution, (3) casting the mixture into a mold; and (4) rapidly freezing and lyophilizing the mixture. The final product contains the elemental iodine generating compounds encapsulated within desiccated fibers of the hydrogel in a dormant state.

An alternative method of manufacturing the hydrogel device without use of a mold is to cast the hydrogel premixed with elemental iodine generating formulations in sheets of from about 0.3 to about 0.5 cm thick, lyophilize the sheets, and then trim the sheets to the desired shape. Trimming is done with any suitable shearing device, knife or blade.

A variety of suitable anti-infective oxidants other than elemental iodine, including hydrogen peroxide, nitric oxide, hydroxyl radical, hypohalites, haloamines, thiocyanogen, and hypothiocyanite may be incorporated into the hydrophobic polymer wound dressing embodiment. The concentration of all solid powdered anti-infective precursors encapsulated within the polymer base should be in the range from about 0.01% to about 16% by weight relative to the polymer mass. The preferred concentration range of halides egressing from the polymer base upon solvation should preferably range from about 1 mM to no more than about 200 mM. The concentration of thiocyanate egressing from the polymer, if encapsulated within the polymer base, should not be less than about 1 micromolar nor exceed about 5 millimolar.

The precursors of the oxidants are contained as solids into a hydrophobic polymer base as discussed above. The hydrogen peroxide generators include nonenzymatic reactants and enzymatic reactants. The nonenzymatic reactants include percarbamide, perborates such as alkali metal perborates, sodium percarbonate; calcium peroxide, benzoyl peroxide, cumyl hydropeoxide, 3-morpholinosydnonimine hydrochloride (SIN-1), and similar peroxy acid precursors and hydrogen peroxide addition compounds in which hydrogen peroxide is a product formed by spontaneous hydrolysis or solvation of the primary precursor compound. Enzymatic reactants include substrate oxidoreductases illustrated as in the following coupled reactions: glucose+glucose oxidase (D-glucose:oxygen 1-oxidoreductase; EC 1.1.3.4) encapsulated as dry solids within polymer base or with enzyme noncovalently or covalently attached to polymer surface using enzyme immobilization techniques known to those familiar with the art (see below); xanthine (or hypoxanthine)+xanthine oxidase (EC 1.1.3.22) similarly incorporated as in the case of the glucose/glucose oxidase (D-glucose:oxygen 1-oxidoreductase; EC 1.1.3.4) reactants; spermine, putrescine, benzylamine (and related amine substrates) of diamine oxidase; and comparable oxidoreductases in which the substrate serves as an electron donor catalyzing reduction of molecular oxygen to yield hydrogen peroxide either as a direct product or via dismutation of superoxide formed as a precursor of hydrogen peroxide formation. The term benzylamine of diamine oxidase should be understood to mean amine:oxygen oxidoreductase [deaminating] [pyridoxal-containing]; EC 1.4.3.6. Enzymes cannot be incorporated into polymers requiring high temperature curing steps, but can be included in the second hydrogel layer of the bilayer embodiment of the wound dressing.

The superoxide, nitric oxide and hydroxyl radical generators include, SIN-1*, S-nitroso-N-acetylpenicillamine (SNAP), and NONOate [N-(2-aminoethyl)-N-(2-hydroxynitrohydrazino)-1,2-ethylenediamine] encapsulated as solids within the polymer base and activated upon wetting of the polymer as generators of NO; xanthine+xanthine oxidase encapsulated as dry solids within the polymer base or with xanthine oxidase noncovalently or covalently attached to the polymer surface, and SIN-1*encapsulated as a solid powder within the polymer base, as generators of superoxide, hydrogen peroxide and hydroxyl radicals. SIN-1 by itself is capable of generating superoxide, hydrogen peroxide, hydroxyl radical, and nitric oxide concomitant with its solvation and subsequent hydrolysis.

Hypohalites can be generated by a polymeric material containing one of the above $H_2O_2$ generators in combination with myeloperoxidase (donor:hydrogen-peroxide oxidoreductase; EC 1.11.1.7) contained within a hydrogel polymer base as the second layer of the bilayer embodiment, or with myeloperoxidase noncovalently or covalently attached to the polymer surface of the hydrophobic polymer layer. In this formulation, hypochlorous acid is formed upon wetting of the polymer in a body fluid due to the ubiquitous presence of chloride ions in solution wherein chloride ion and $H_2O_2$ serve as substrates of myeloperoxidase in forming hypochlorite. Alternatively, hypoiodite, or hypobromite, both of which also exhibit strong anti-infective activities, may be formed with inclusion of the alkali salts of iodine and bromine, respectively, encapsulated as dry powders within the polymer base.

Haloamines can be generated by encapsulation of hypohalite generators in the base polymer in combination with primary or secondary amines such as taurine, histidine, spermine, lysine, glycine and similar aliphatic and cyclic primary and secondary amines which upon exposure to hypohalites form the corresponding long-lived haloamines such as taurine chloramine, histidine chloramine, spermine chloramine, and the like.

Thiocyanogens and hypothiocyanites can be generated by encapsulation of the above $H_2O_2$ generators within the polymer base in combination with myeloperoxidase (donor:hydrogen-peroxide oxidoreductase; EC 1.11.1.7), lactoperoxidase (donor:hydrogen-peroxide oxidoreductase; EC 1.11.1.7), horseradish peroxidase (donor:hydrogen-peroxide oxidoreductase; EC 1.11.1.7), or other donor:hydrogen peroxide oxidoreductase, encapsulated within or attached covalently or noncovalently to the polymer surface, and a dry powder alkali salt of thiocyanate, wherein $H_2O_2$ and thiocyanate serve as substrates of the peroxidase in the formation of thiocyanogen, or its hydrolysis product, hypothiocyanite, in fluid coming into contact with the polymer upon solvation and egress of the encapsulated reactants.

Immobilization of Enzymes by Covalent or Noncovalent Methods to the Polymer Surface In the embodiments having enzymatic reactants, the enzymes can be attached to the polymeric material using conventional methods. For example, methods for the covalent and noncovalent attachment of enzymes to silicone and other hydrophilic and hydrophobic polymers include diazotization, amide bond formation, alkylation and arylation, amidation as well as ionic charge associations and hydrophobic binding as described in detail in:

Miller, R. E. (1972) Attachment of Enzymes to Siliceous Materials, U.S. Pat. No. 3,669,841.

Zaborsky, O. R. (1974) in, *Immobilized Enzymes*, CRC Publishing, Cleveland, OH.

Avrameas, S. et al. (1990) Immobilization of Active Protein by Cross-Linking to Inactive Protein. U.S. Pat. No. 4,970,156.

Okamura, S. et al. (1976) Method for Manufacturing Medical Articles Composed of Silicone Rubber Coated with Collagen. U.S. Pat. No. 3,955,012.

Rohrback, R. P. et al. (1980) Support Matrices for Immobilized Enzymes. U.S. Pat. No. 4,206,259.

Hearn, M. T. (1987) 1,1'-Carbonyldiimidazole-Mediated Immobilization of Enzymes and Affinity Ligands. Meth. Enzymol. 135, 102–117.

Miron, T. and Wilchek, M. (1987) Immobilization of Proteins and Ligands Using Chlorocarbonates. Meth. Enzymol. 135, 84–90, all of which (together with the other documents cited in this application) are incorporated by reference in their entireties.

Wetting of the polymer containing the encapsulated reactants during attachment of the enzyme to the surface of the polymer is not critical, nor does it defeat the performance of the polymer in releasing anti-infective activity. The period required for covalent and/or noncovalent attachment of the enzyme catalyst is of a brief duration, generally over a period of a few hours, wherein the solvation of encapsulated reactants is minimal relative to the reservoir of reactants retained within the polymer. Furthermore, by judicious choice of the attachment method the pH, oxygen tension, or other critical substrate, can be manipulated to preclude formation of reactive products during enzyme attachment. In the case of donor:oxygen oxidoreductases (for example, glucose oxidase (D-glucose:oxygen 1-oxidoreductase; EC 1.1.3.4)), attachment of the enzyme under anaerobic conditions using aqueous solutions purged of oxygen deprives the enzyme of oxygen as a co-substrate in the formation of hydrogen peroxide, and therefore prevents premature formation of anti-infective products. Similarly, the exclusion of a halide source while coupling myeloperoxidase precludes formation of a hypohalite during the immobilization of myeloperoxidase to the surface of the polymer base. Upon completion of the enzyme immobilization step, the polymer can be dried by air, or by blotting on a suitable absorbent such as paper or felt, so that the residual moisture left on the surface precludes any further solvation of encapsulated reactants.

In certain instances where the chemistry precludes attachment of the enzyme to the surface of the polymer directly because of too rapid of release of reactants from the polymer during the attachment phase, and where entrapment of enzyme within the polymer base is deemed too costly or inefficient, the enzyme can instead be immobilized to a second, thin polymer film lacking reactants. The latter film containing immobilized enzyme can be attached to the implant polymer containing encapsulated reactants in the form of an elastic band, grid, or patch, bringing the enzyme in close proximity to the surface of the polymer containing encapsulated reactants. In this manner the enzyme serves to catalyze reactants into anti-infective products as the reactants solvate and egress to the surface of the implanted polymer.

From the foregoing descriptions it is thus evident that in the bilayer embodiment of the wound dressing invention that different combinations of the two layers may be chosen depending upon the wound site application. The upper and lower layers may be fabricated of the same polymer base such as acrylamide, or a combination of acrylamide in one layer (vis., the upper layer) and a cotton fiber, acylamide and a hydrogel, or alternatively acylamide and a silicone or polyurethane layer. The combinations which can be used in this bilayer embodiment provides for flexibility in the design of the wound dressing while allowing the essential components to be stored in a stable form prior to use. For long term applications and minimal exposure to iodine, the upper layer should preferably be made of a hydrophobic polymer in which the iodide salts are entrapped within the polymer base as immiscible solids wherein they can leach out slowly into the wound site allowing for a controlled rate of iodine production. The release rate is proportional to the initial loading dose of the salts dispersed within the polymer base, and the specific polymer used to encapsulate the ground salts.

EXAMPLE 1

This example illustrates the incorporation of iodide into a silicone disc device and long term release rates of iodide upon submersion and washing of the device in buffer. Finely ground sodium iodide (3 g), prepared in a mortar and pestle, was mixed into 10 g of RTV silicone elastomer (polydimethylsiloxane) to which was also added 1 g dibutyl tin dilaurate catalyst stock solution. The ground crystalline sodium iodide powder recovered from the mortar and pestle was added last to the polymer base after thorough mixing of the catalyst into the silicone, and the silicone then poured into 5.0 cm diameter Petri dishes to a depth of ~0.3 cm in thickness. After 24 hrs, the cured disc was removed, thoroughly rinsed in 10 mM sodium phosphate buffer, pH 5.6, made up in 150 mM NaCl, and then placed into a 150 ml beaker containing 10 ml of the same buffer. At varying intervals (see FIG. 3), including an initial t=0 measurement, buffer was drained from the beaker and device, and set aside for analysis of iodide content. The release of iodide was measured after mixing $H_2O_2$ (~56 mM) with 1 ml aliquots of the sample washings. The assay tracked formation of elemental iodine at 350 nm in a Shimadzu UV-265 double beam spectrometer against a standard calibration curve constructed with known quantities of sodium iodide made up in the same buffer and worked up in the same manner. Fresh 10 ml aliquots of buffer were washed over the device for analysis of subsequent release of iodide over the next interval, and this process was repeated over a period of approximately 30 days. In between, the device immersed in buffer was left on a shaking rocker platform at room temperature. Precautions were taken to minimize evaporation between sampling intervals by covering the top of the beaker with plastic wrap.

Figure 3:
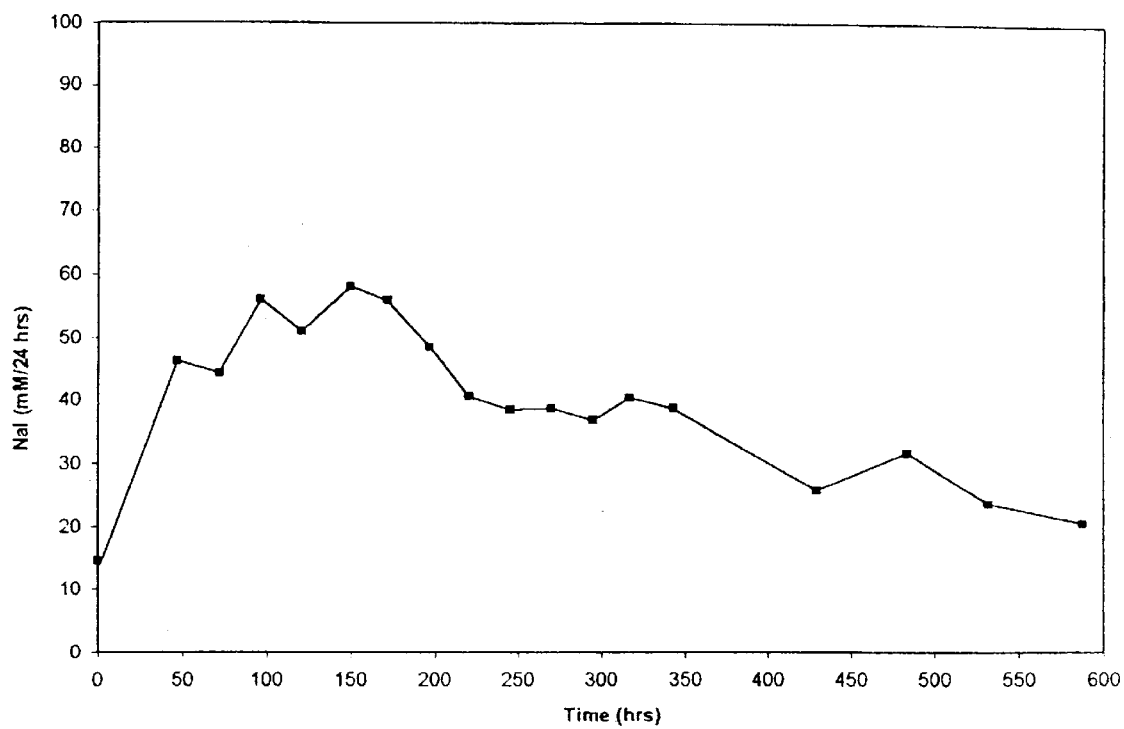
FIG. 3 illustrates a graph of the sustained release of NaI from silicone fabricated device submerged and continuously washed in 10 mM sodium phosphate, 150 mM NaCl, pH 5.6 (see Example 1).

FIG. 3 shows that sodium iodide, incorporated at a ratio of solid to elastomer of ~30% into the polymer base of the fabricated device, allowed for the release of iodide (upon immersion and sequential changes in buffer). The peak iodide release was at around 50 to 60 mM (in a fluid volume of 10 ml buffer per washing interval). The capacity of the device to restore iodide to this level with sequential changes in buffer remained relatively constant over the first 350 hrs, and then declined to ~20 mM by around 600 hrs of continuous immersion and rinsing of the device in buffer. Calculations of iodide recovery, relative to the iodide initially available in the device, indicated that by 600 hrs of continuous immersion and washing under the above conditions ~90% of the iodide was leached from the device.

EXAMPLE 2

This example illustrates iodate reduction and conversion to elemental iodine and microbicidal tests on fabricated devices encapsulated with iodate and iodide in silicone-based polymer. Based upon evidence that many body fluids are rich in reducing compounds, antioxidants, and the like, alternate methods of generating elemental iodine de novo from iodide and iodate were investigated using Brain Heart Infusion (BHI) media to mimic complex body fluid conditions. BHI is a rich source of reducing compounds of the type found in body fluids. The formation of elemental iodine de novo from iodide and iodate in BHI media was confirmed by titrating solutions of BHI with incremental additions of iodide and iodine pentoxide (the anhydride of iodate), either in combination, or with iodine pentoxide alone. Following additions of trace amounts of iodide in combination with iodine pentoxide (total iodine<1 mg/ml broth media), the BHI media took on an intense yellow-orange hue, indicative of $I_3^-$ formation (e.g., formation of elemental iodine and its complexation with iodide ion). The presence of elemental iodine was confirmed by extraction of BHI media titrated in this manner with chloroform, which revealed the characteristic intense violet color of elemental iodine associated with its partitioning into the lower chloroform layer (absorbance max, 508 nm). These data were interpreted as evidence of robust elemental iodine production arising by the reductive conversion of iodate to elemental iodine, but also as evidence that iodate was oxidizing added iodide into elemental iodine in accordance with theoretical expectations based upon the chemistry of iodate.

This latter conclusion was based upon the observation that addition of trace amounts of iodate (~0.5 mg/ml in the form of iodine pentoxide) alone to BHI media did not alter the coloration to the media. Further additions in excess of ~1 mg/ml, however, ultimately led to a similar set of findings to those seen with additions of iodide and iodate to the broth media. These results were interpreted as evidence of conversion of iodine pentoxide to iodate, reduction of iodate to iodide by reducing equivalents present in BHI, and subsequent oxidation of iodide to elemental iodine by further additions of iodine pentoxide to the media. The interconversions appeared complex and dependent upon the rate of reduction of elemental iodine and iodate to iodide by reducing equivalents in the media, as opposed to the opposing rates of oxidation of iodide to elemental iodine caused by the presence of iodate in the broth media and the rate at which iodine pentoxide spontaneously hydrolyzes to iodate.

Disc shaped silicone devices were prepared as in example 1, except formulations of iodide and iodine pentoxide, or iodine pentoxide alone and in combination with NaCl as a carrier were incorporated into the silicone. The formulations were aimed at testing the device's capacity to produce microbicidal activity upon submersion in BHI broth media. Specifically, sodium iodide (3 g) was ground to a fine powder under anhydrous conditions with iodine pentoxide (1 g) and dispersed in 10 g of silicone elastomer premixed with silicic ester dibutyl tin dilaurate catalyst, then poured into 50 mm Petri dishes and processed as in Example 1. Smaller discs were cut from the device using a hole punching tool in producing silicone patches of ~6 mm diameter. These were placed in BHI media, previously adjusted to pH 4.0, at 1 patch per ml, and the BHI media containing the patches then inoculated with test organisms, as noted in Table 2 (below).

A similar device was prepared using NaCl in place of sodium iodide at 2 g per 10 g of silicone polymer base. Patches from this device were also tested for microbicidal activity upon introduction to inoculated BHI media as described in Table 3 (below). As expected, all of the patches formulated with both iodide and iodine pentoxide produced an intense yellow coloration immediately upon contact with BHI media, indicative of instantaneous elemental iodine formation. Patches with only iodine pentoxide present had no discernible effect on the coloration of the BHI media.

TABLE 2

Microbicidal Activity of iodide/iodate Encapsulated Silicone Patches - Recovered CFU/ml Following Inoculation in BHI Media and Saline.

| Organism | Inoculation Time (hrs) | Inoculation Medium | |
|---|---|---|---|
| | | Saline | BHI, pH 4.0 |
| C. albicans | 0 | 66000 | 40000 |
| | 24 | <10 | <1000 |
| | 48 | nd | <10 |
| L. casei | 0 | 500000 | 500000 |
| | 24 | <10 | <1000 |
| | 48 | nd | <10 |

Incubations conducted at 35° C.
nd = not determined.

TABLE 3

Microbicidal Activity of iodine pentoxide Encapsulated Silicone Patches - Recovered CFU/ml Following Inoculation of Test Media.

| Organism | Inoculation Time (hrs) | Inoculation Medium | |
|---|---|---|---|
| | | Saline | BHI, pH 4.0 |
| C. albicans | 0 | 140000 | 100000 |
| | 3.5 | <10 | <1000 |
| | 22 | <10[a] | <10[b] |

Incubations conducted at 35° C.
nd = not determined.
[a]chloroform extraction on residual culture media-no appearance of violet coloration.
[b]chloroform extraction on residual culture media-strong violet coloration indicative of elemental iodine presence.

Figure 4:
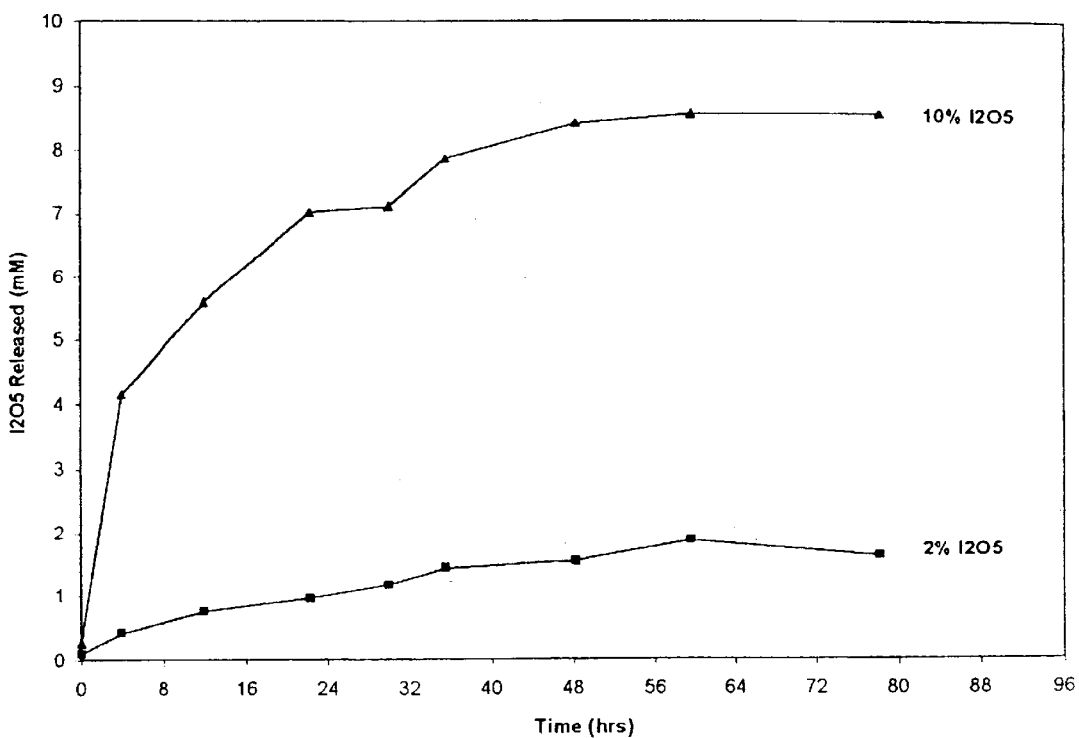
FIG. 4 illustrates a graph of the kinetic release of encapsulated $I_2O_5$ from silicone fabricated device at various intervals after submersion in 100 mM sodium citrate, pH 4.0, at 2% and 10% $I_2O_5$ formulations by mass (see Example 2).

FIG. 4 also shows the kinetic release of iodine pentoxide from discs prepared in the same manner as in the microbicidal studies summarized in Table 3. The discs were suspended in 100 mM sodium citrate, pH 4.0, at 1 patch per ml, but using different mass concentrations relative to the polymer based in fabricating the silicone device. The concentration of iodate released was proportional to the mass encapsulated into the polymer (FIG. 4). In these experiments the total salt (NaCl) mixed into the silicone polymer was held constant at 30% and comprising iodine pentoxide and NaCl as necessary to maintain a constant salt:polymer ratio, but at concentrations of iodine pentoxide per unit polymer mass of 2% and 10%, respectively. Complex media, such as BHI, had no discernable impact on the solvation and diffusion rates of iodine pentoxide as similar rates of iodine pentoxide release were seen substituting BHI media in place of citrate buffer.

The data from Tables 2 and 3 show that elemental iodine mediated killing of the microorganisms tested. These data were generated as a result of fabricating the device with varying concentrations of iodide in combination with iodine pentoxide and placing patch samples from the device within the BHI media rich in reducing compounds, or saline. The organisms supplied their own source of reducing compounds to the device patches. The levels of iodate required for effective microbicidal activity appeared to be <<5 mM, based upon measurements of iodate released from the patches, and by an examination of the killing interval after introduction of the patches to inoculated cultures (see, for example, Tables 2 and 3, and FIG. 4). For example, the data in Table 3 indicates effective killing occurred within 3 to 4 hours of exposure to the iodine pentoxide patches. Assuming all of the iodate released into the media could be converted to elemental iodine, this suggests an upper limit of iodine in the BHI media could not theoretically exceed ~125 mg/dl (e.g., 5 mM elemental iodine). The elemental iodine concentration was found experimentally to be far less than this calculation (see below).

These data indicate that elemental iodine concentrations required to affect microbial killing are generally <<0.01% (that is, as much as two orders of magnitude below the iodine content of povidone-iodine solutions). The lower elemental iodine concentrations required and produced by the inventive device, relative to iodophor vehicles such as povidone-iodine, are attributed to the fact that iodate was released slowly over a period of time using the fabricated silicone device as the vehicle for its presentation in solution. Further, recycling of iodate to iodide, and then back to elemental iodine, likely occurred continuously as fresh iodate continued to egress from the device and encounter reducing compounds, and iodide recycled from elemental iodine formed in an earlier cycle, in its path. Thus, even trace quantities of iodide can be envisioned to recycle in the reaction media until taken up by the microbial cell in the form of elemental iodine, whereupon killing of the microbe then ensues.

EXAMPLE 3

This example illustrates the microbicidal activity and optimization of iodate and iodide formulations for de novo formation of elemental iodine. Experiments were performed to optimize formulations used in fabricating the inventive device formulated with silicone elastomer. Finely ground iodate and iodide were mixed into silicone elastomer in various loadings relative to the elastomer. The polymer was allowed to cure with dibutyl tin dilaurate catalyst additions, and then devices were prepared (0.6 cm diameter 0.3 mm thick) using "hole punch" patches from the disc shaped device to test for microbicidal activity using $C.$ $albicans$ inoculated BHI. BHI media was adjusted to pH 4.0 with HCl, and an inoculum of approximately $1 \times 10^5$ CFU/ml $C.$ $albicans$ (ATCC 66027) was added to the broth media. Patches obtained from the fabricated device were suspended in the inoculum at 1 patch/ml. At varying intervals, aliquots of the inoculum, incubated at 35° C. in air, were subcultured to sheep blood agar plates and incubated for an additional 24 hours at 35° C. in air to determine the effect of the varying formulations on the $C.$ $albicans$ inoculums.

Patches obtained from devices formulated in the range of 1% to 16% by weight iodide alone relative to silicone elastomer (total salt, 30% by weight with the difference made up with NaCl as a carrier salt) showed no microbicidal activity. Patches made up in the same manner, but with iodate alone ranging from 0.5 to 12% by weight, showed no microbicidal activity against $C.$ $albicans$ at 24 hours exposure. However, in the range of 4 to 12% iodate a 1 to 2 log decrease in growth at 48 hours exposure, and <10 CFU/ml were found with 72 hours exposure.

Patches obtained from silicone devices made up with varying weights of iodate ranging from 2 to 4% by weight, and iodide ranging from 0.1 to 0.25% by weight combinations (additional weights of NaCl added to bring the final salt weight relative to silicone to 30%), showed no microbicidal activity. However, with increasing weights of iodide in excess of 0.5% by weight in the presence of 4% by weight or greater iodate, complete killing of $C.$ $albicans$ occurred within 24 hours of submersion of the patches within the BHI inoculums. Therefore, the lower limit of the formulation needed to effect killing within 24 hours exposure in complex BHI media amounted to approximately 4% iodate, 0.5% iodide and 24.5% NaCl salt (ground to <200 microns) all by weight suspended in the silicone base used in fabricating the devices. Further tests revealed that formulations varying from 4% to 8% iodate, and from 2% to 16% iodide all by weight were very efficient in killing $C.$ $albicans$ with complete killing occurring in less than 4 hours of submersion of the silicone patches within the BHI inoculums.

PVP was also found to improve the stability of the silicone formulation by acting as both a desiccant and an iodophor, such as by preventing moisture from the atmosphere from prematurely activating the iodide salts mixed into the silicone elastomer. By inclusion of from about 1% to about 10% finely ground PVP by weight together with iodate and iodide in fabricating the microbicidal disc shaped device, the final device obtained after curing of the elastomer showed less tendency to express elemental iodine upon exposure to air over time. No adverse effects of including PVP in the salt formulations were observed with regard to alteration of the device's microbicidal activity. The optimal iodide salt formulation based upon the patch tests used was 8% iodate, 2% iodide and 10% PVP with omission of NaCl from the final salt mixtures. The latter "carrier" salt was found to provide no obvious benefits in fabricating the device, nor did it appear to have any significant effect on the release rates of the salt formulations encapsulated within the silicone device.

Figure 5:
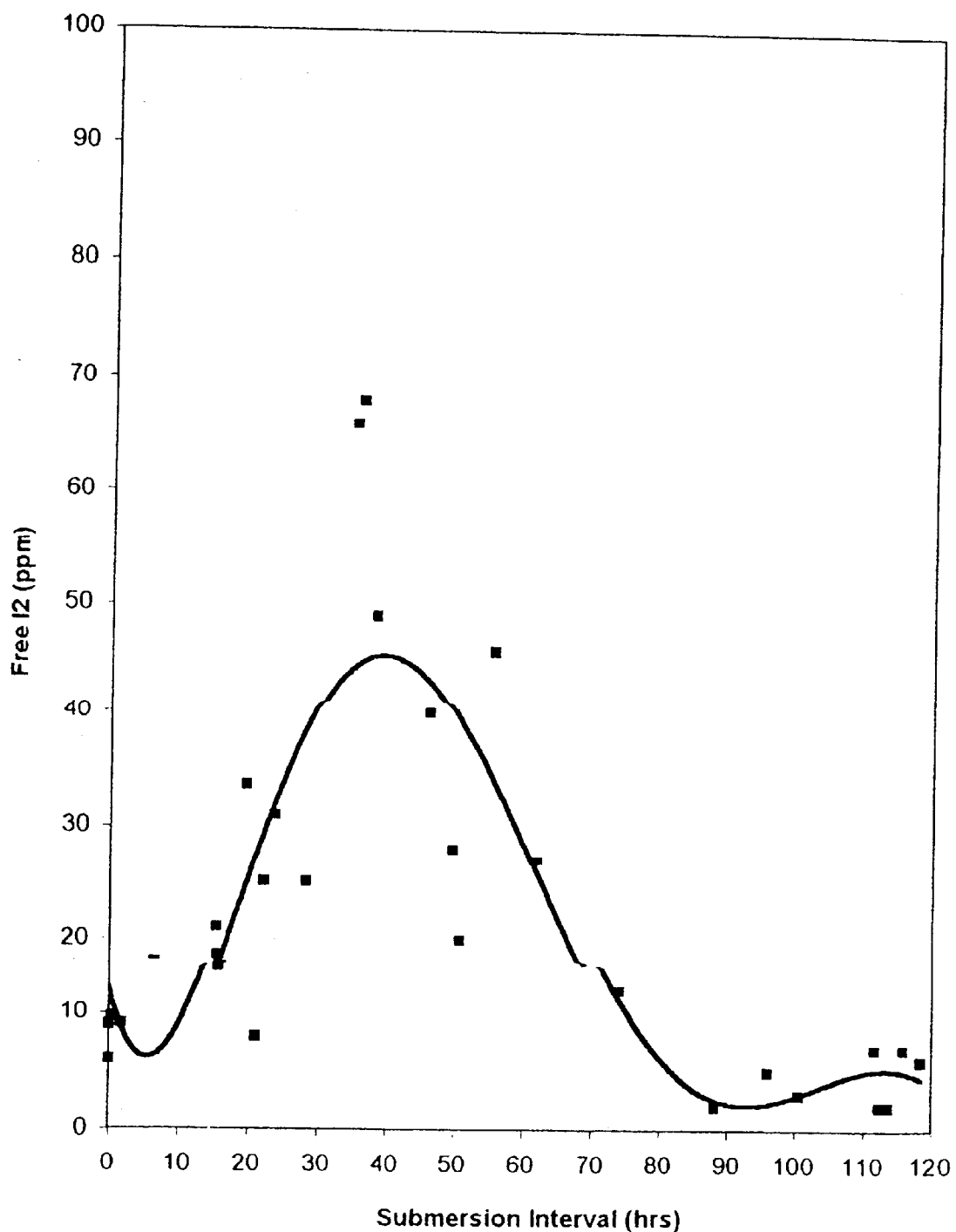
FIG. 5. illustrates a graph of the recovery of free $I_2$ at varying intervals following submersion of silicone fabricated device in 100 mM sodium citrate, pH 4.0, in a formulation consisting of 2% $I^-$, 8% $IO_3^-$ and 10% PVP by mass relative to silicone elastomer (see Example 3).

Concomitant with the microbicidal killing studies, measurements were made on the formation of elemental iodine during submersion of the patches in citrate buffered solutions. FIG. 5 shows the accumulation of elemental iodine in the citrate buffer tracked over a period of approximately five days submersion of the iodate/iodide/PVP loaded patches (1 patch/ml). Each point represents an experiment in which three patches in 3 ml 100 mM citrate, pH 4.0, were submerged for the interval shown, and then an aliquot (1 ml) of the buffer solution assayed for residual elemental iodine. Elemental iodine was quantitated by extracting citrate buffer aliquots in chloroform (1 ml), and reading the absorbance at 508 nm against a calibration curve constructed with crystalline elemental iodine made up in chloroform at known concentrations expressed in ppm elemental iodine. While there was significant variability in the generation of free elemental iodine over the five day interval examined, elemental iodine ranged from a low of approximately 2 ppm to a high of 70 ppm in this series of experiments. The maximum elemental iodine level peaked around 36 to 48 hours after submersion of the patches in citrate buffer.

EXAMPLE 4

This example illustrates the fabrication of a hydrogel device embodiment that is activated upon contact with aqueous fluids. Two percent "medium viscosity" sodium alginate was mixed with an equal volume of 2% Carbopol 971 (B. F. Goodrich) (cross-linked polyacrylate) to yield a composite 1% viscous gel solution, pH 3.95, made up in equivalent weights of alginate and Carbopol. This gel mixture was chilled to ~4° C. 100 mM potassium iodide made up in water was then mixed thoroughly into the gel to yield a final concentration of 1 mM potassium iodide. An equivalent amount of 100 mM sodium iodate was rapidly mixed into the gel to yield a gel mixture comprised of 1 mM sodium iodate, 1 mM potassium iodide, 1% alginate and 1% Carbopol 971. This mixture was quickly frozen at −70° C., lyophilized overnight under vacuum, and yielded a fine, highly porous, lightweight, sponge-like product, red-brown in appearance. The sponge-like product was cut into various shapes and left in sealed containers (to keep out moisture) at room temperature without loss of its nascent elemental iodine generating capacity (that is, upon solvation in aqueous solutions).

Upon addition of water to the sponge-like material, its color changed almost instantly from red-brown to an intense canary-yellow, revealing rapid formation of nascent elemental iodine complexed to iodide in the form of $I_3^-$, and it thickened into a viscous hydrogel. The presence of nascent elemental iodine was confirmed by extraction in chloroform and verification by spectral scanning of the final extract (e.g., absorbance max, 508 nm; product lost upon addition of excess reducing agents to the rehydrated gel). Various shapes of the sponge-like product were also prepared by freezing gel mixtures immediately after addition of iodate and iodide, and before significant elemental iodine was allowed to form.

While the rate of elemental iodine formation in the same gel mixtures was very much slower when first prepared in aqueous form for freezing, following freezing and lyophilization, iodate and iodide rapidly produced elemental iodine, as noted, within seconds of coming into contact with aqueous solutions. This was determined to be the result of the concentrating effect of lyophilization, such that solvation allowed for much higher concentrations of iodate and iodide to interact with one another in generating elemental iodine then was possible prior to the freezing and lyophilization. After lyophilization, in the absence of water, iodate and iodide were not free to interact with one another pending their solvation. Hence, this embodiment of the invention, referred to as the hydrogel device, allowed for incorporation of all of the essential reactants within a single matrix (e.g., the hydrogel polymer).

A hydrogel embodiment device was also prepared using glucose oxidase (D-glucose:oxygen 1-oxidoreductase; EC 1.1.3.4) (10 µg/ml) and horseradish peroxidase (donor:hydrogen-peroxide oxidoreductase; EC 1.11.1.7) (3 µg/ml) mixed into a 1% alginate-Carbopol gel suspension made up in water at room temperature to which potassium iodide at a final concentration of 2 mM was added. The gel mixture was frozen and lyophilized as in the iodate/iodide embodiment. The sponge-like product (in this case) exhibited an off-white color with a tinge of yellow, and could be stored for several weeks at room temperature without loss of nascent elemental iodine generating activity initiated by the addition of glucose (~50 mg/dl). Controls in which water was added in place of glucose solution showed no elemental iodine formed. In both instances, the sponge-like product quickly solvated to a viscous, mucous-like hydrogel. Elemental iodine was confirmed by recovery of elemental iodine in chloroform extracts similar to hydrogel delivery devices formulated with iodide and iodate. The concentration of glucose used to activate the glucose oxidase/horseradish peroxidase formulated delivery device was not particularly critical in that solutions as low as 10 mg/dl and higher concentrations in the range of 100 mg/dl, when added to the desiccated gel, initiated nascent elemental iodine formation.

Both embodiments of hydrogel formulations cited in this example showed formation of nascent elemental iodine ranging from a low of a few ppm to an upper limit in the range of 100 ppm.

The elemental iodine formation was commensurate with the concentrations of glucose oxidase/horseradish peroxidase, or iodide and iodate incorporated into the hydrogel prior to freezing and lyophilization of the gel mixtures. Elemental iodine was seen to persist in the thick gel mixtures for a period of approximately 8 to 10 hours after which it tapered off to undetectable levels.

Figure 6:
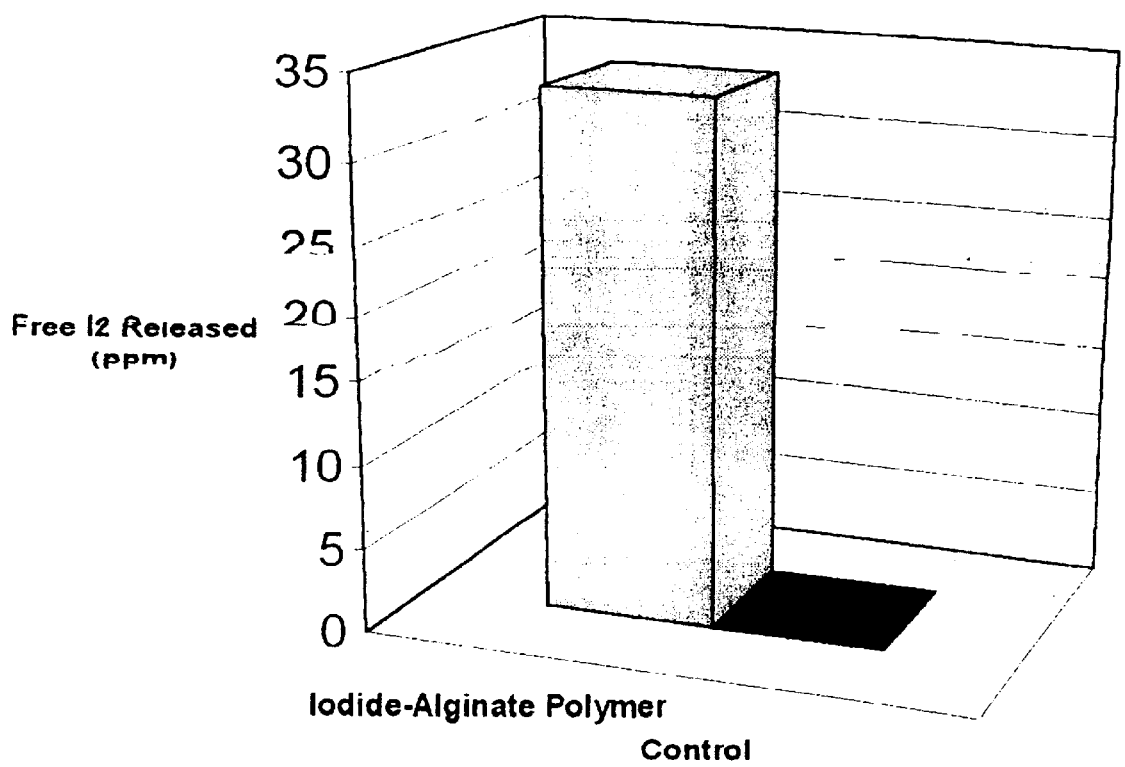
FIG. 6. illustrates a graph of the de novo formation of free $I_2$ released from $I^-/IO_3^-$ encapsulated 1% "high viscosity" alginate hydrogel upon submersion of fabricated device in 100 mM sodium citrate, pH 4.0. Control used same hydrogel composition excluding $I^-/IO_3^-$ from formulation (see Example 4).

FIG. 6 shows de novo formation of elemental iodine upon solvation of a lyophilized 1% "high viscosity" pH 4.0 alginate inventive device embodiment prepared in the form of a cylinder. The initial formulation comprised a 2 mM potassium iodide solution and a 2 mM sodium iodate solution. The gel was cast in 100 (length)×0.6 cm (internal diameter) tubes in the frozen state, lyophilized and cut longitudinally into 1 cm sections. Control gel was prepared in the same manner but with omission of iodide and iodate from the final mixtures. Elemental iodine was measured following 20 minutes submersion of the alginate formulation (1 cm lengths) in 1 ml 100 mM citrate buffer, pH 4.0. Values shown (FIG. 6) represent the average of triplicate experiments compared to control results using alginate formulated in the same manner except for the exclusion of iodide and iodate from the polymer matrix. Concomitant with the in situ formation of elemental iodine, the gel swelled to a viscous, mucous-like, hydrogel characteristic of its original composition prior to lyophilization.

EXAMPLE 5

Figure 7:
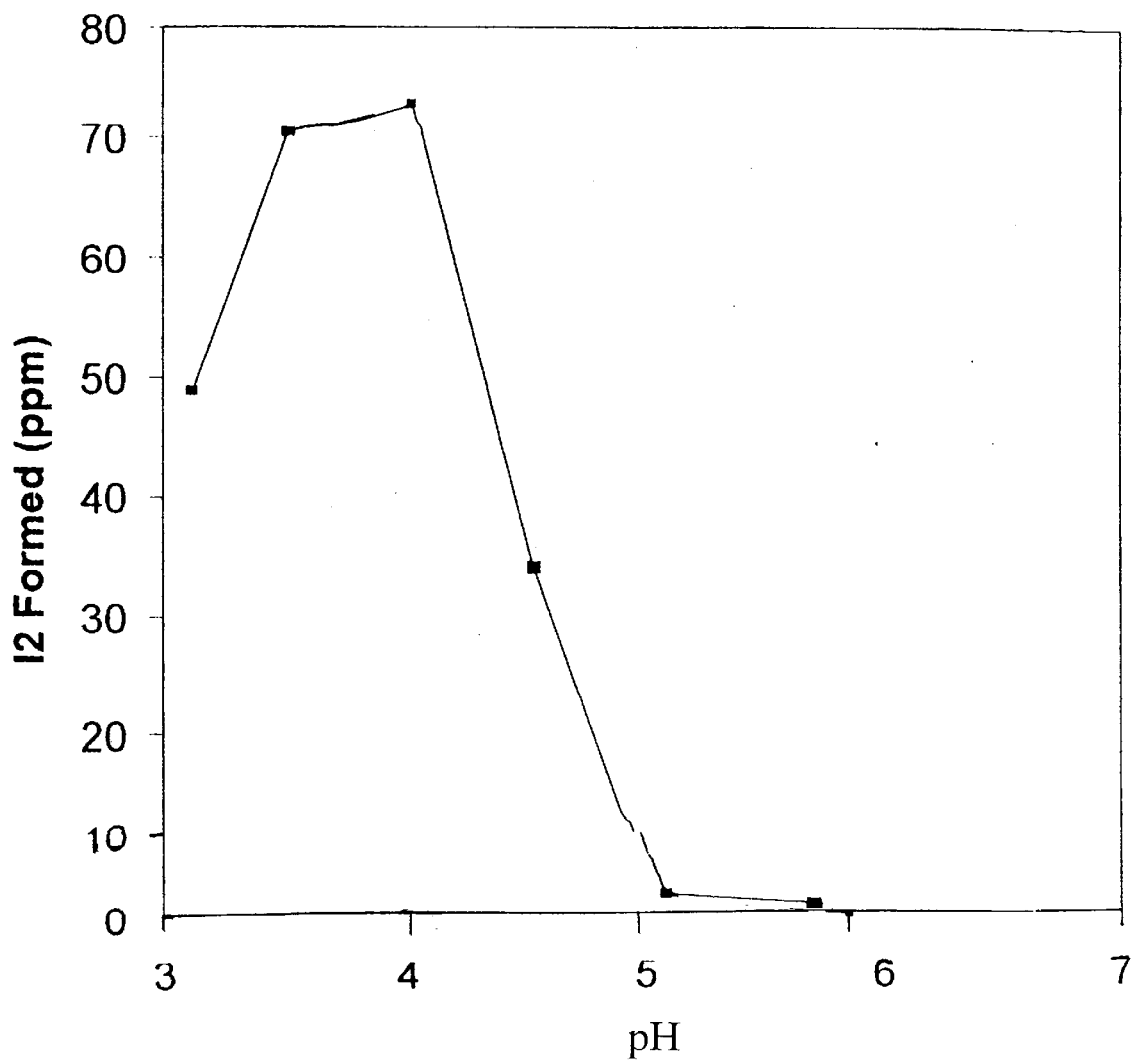
FIG. 7. illustrates a graph of the effect of pH on nascent formation of free iodine released from silicone membranes containing encapsulated potassium iodide and sodium iodate (see Example 5).

FIG. 7 shows the effect of varying the pH of buffered citrate solutions (50 mM) on the rate of free elemental iodine formation using potassium iodide and sodium iodate as precursors. Iodine was quantitated as the triiodide complex formed by transfer of aliquots of test reaction mixtures to stock 10 mM potassium iodide made up in distilled water measured at 350 nm on a double-beam UV-265 double beam Shimadzu spectrometer. A calibration curve was prepared using crystalline iodine dissolved in the same stock potassium iodide solution. Citrate buffered solutions were made up to known pH values as indicated, determined by titration and measurement on a standard pH meter. Aliquots of the citrate buffered solutions were mixed with silicone discs impregnated with a mixture of 2% potassium iodide and 10% sodium iodide (by weight relative to the disc). Following varying incubation periods, aliquots of the test solutions were analyzed for formation of elemental iodine as noted above from which a pH profile was constructed showing the rate of free iodine formation versus proton concentration. The optimal pH for iodine formation was observed to be approximately 4.5 regardless of the incubation interval. Samples were monitored for iodine formation from approximately 10 minutes up to 24 hours after initiation of the reaction. FIG. 7 is typical of the pH profiles observed reflecting accumulated free iodine approximately 4 hours after initiation of iodine formation.

While this invention has been described in conjunction with specific embodiments and examples, it will be apparent to a person of ordinary skill in the art, having regard to this disclosure, that equivalents of the specifically disclosed materials and techniques will also be applicable to this invention; and such equivalents are intended to be included within the following claims.

What is claimed is:

1. A wound dressing having anti-infective activity when applied to a wound site in a patient, comprising
   a) a crosslinked polymeric sheet impermeable to bacteria, catalase, and heme proteins; and
   b) a formulation free of tri-iodide, contained within the polymeric sheet, wherein the formulation generates elemental iodine upon chemical reaction with a substrate present in wound fluid from the wound site which permeates the polymeric sheet.

2. The wound dressing of claim 1 where the polymeric sheet is impermeable to reactants in the wound fluid that are capable of reacting with any hydrogen peroxide and oxygen formed by the chemical reaction of the formulation and substrate.

3. The wound dressing of claim 1 where the polymeric sheet comprises polyacrylamide.

4. The wound dressing of claim 1 where the formulation is stable at least until contacted by the substrate.

5. The wound dressing of claim 4 where the formulation comprises an oxidoreductase that reacts with the substrate on contact therewith.

6. The wound dressing of claim 5 where the oxidoreductase is glucose oxidase.

7. The wound dressing of claim 5 where the formulation comprises an iodide, glucose oxidase, and a peroxidase, and the substrate is glucose.

8. The wound dressing of claim 7 where the formulation is present in an amount sufficient to cause the release of about 5 ppm to about 100 ppm of elemental iodine from the sheet into the wound fluid.

9. The wound dressing of claim 6 where the formulation comprises an iodide, an oxidant, and glucose oxidase, and the substrate is glucose.

10. The wound dressing of claim 9 where the formulation comprises an iodide, an oxidant, glucose oxidase, and catalase, and the substrate is glucose.

11. The wound dressing of claim 4 where the formulation is selected from the group consisting of a formulation comprising iodate and protons, and a formulation comprising iodate and a proton donor generator.

12. The wound dressing of claim 11 where the formulation comprises a formulation comprising iodate and protons at a concentration measured in pH units of between about pH 2 and about pH 5.

13. The wound dressing of claim 11 where the formulation comprises a formulation comprising iodate and a proton donor generator selected from the group consisting of an oxidoreductase, a lipase, and an esterase.

14. The wound dressing of claim 1 where the formulation comprises an iodide, an oxidant, glucose oxidase, and catalase.

15. The wound dressing of claim 14 where the oxidant is an iodate.

* * * * *